(12) United States Patent
Wagner

(10) Patent No.: US 8,730,462 B2
(45) Date of Patent: *May 20, 2014

(54) REFRACTOMETRY SYSTEM AND METHOD

(71) Applicant: Rudolph Research Analytical Inc., Hackettstown, NJ (US)

(72) Inventor: Jeff Wagner, Long Valley, NJ (US)

(73) Assignee: Rudolph Research Analytical, Hackettstown, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 13/936,297

(22) Filed: Jul. 8, 2013

(65) Prior Publication Data

US 2013/0293875 A1 Nov. 7, 2013

Related U.S. Application Data

(63) Continuation of application No. 13/071,899, filed on Mar. 25, 2011, now Pat. No. 8,605,271.

(51) Int. Cl.
*G01N 21/41* (2006.01)

(52) U.S. Cl.
USPC .......................................................... 356/128

(58) Field of Classification Search
USPC .......................................................... 356/128
See application file for complete search history.

(56) References Cited

U.S. PATENT DOCUMENTS

| 2002/0154311 | A1* | 10/2002 | Ivarsson | 356/445 |
| 2005/0200852 | A1* | 9/2005 | Kimura | 356/445 |
| 2009/0213382 | A1* | 8/2009 | Tracy et al. | 356/445 |

* cited by examiner

*Primary Examiner* — Tu Nguyen
(74) *Attorney, Agent, or Firm* — Kaplan, Breyer, Schwarz & Ottesen, LLP

(57) ABSTRACT

A critical-angle refractometer which utilizes an in image of light reflected from an optical interface with a vessel containing a sample under test to determine an optical property of the sample, sample properties are evaluated to prevent improper testing of the sample. This evaluation includes establishing reflectance information associating the amount of reflection with locations in the image; and utilizing a plurality of properties of the reflectance information to determine if the vessel contains a proper sample under test.

11 Claims, 3 Drawing Sheets

REFRACTOMETRY SYSTEM AND METHOD

This application is a Continuation of U.S. patent application Ser. No. 13/071,899, filed Mar. 25, 2011, entitled "Critical-Angle Refractometry" then entire disclosure of which is incorporated herein by reference.

BACKGROUND OF THE INVENTION

The present invention relates generally to refractometry and, more particularly, concerns a method and apparatus for improving the accuracy and reliability of critical-angle refractometry measurements.

The purpose of a refractometer is to measure the refractive index of a sample material M, for example, a liquid. A prior art critical-angle refractometer is shown schematically in FIG. 1. The liquid sample M is typically contained in a dish in which one surface of an optical prism P, having a high index of refraction, forms the floor of the dish. Rays of light R from a Light Source S are focused by a Lens L1 into prism P. It is characteristic of the interface between two disparate optical media that a light beam entering the interface will be, in part, refracted or bent upon traversing the interface, and it will be, in part, reflected from the interface. However, for any interface, there is a "critical-angle" such that a light beam incident on the interface with that or a greater angle to the normal will be totally reflected. The critical angle is defined by Equation (1).

$$\sin(\text{critical angle}) = (\text{refractive index of sample})/(\text{refractive index of prism}) \quad (1)$$

By design of the prism/sample interface I in FIG. 1, rays R incident on interface I are at least partially reflected therefrom. The reflected rays exit the prism and are directed by a lens L2 onto a linear optical detector O. The detector O is a linear array of light sensitive pixels, each of which produces an electrical signal proportional to the level of light incident on it. Each pixel receives a bundle of light rays that reflect from interface I at a particular angle of incidence. If this angle of incidence is greater than the critical angle, then 100% of the rays in that bundle are reflected from the interface I. This is called total internal reflection (TIR). If this angle of incidence is less than the critical angle, then the rays are only partially reflected by the prism/sample interface, because a portion of the light is refracted into the liquid sample and, ideally, does not reach the detector. A pixel receiving partially reflected light will sense a lower intensity of light than a pixel receiving totally reflected light. The light intensity pattern on the array of pixels therefore provides a map of the amount of reflection at the prism/sample interface of the bundle of light beams corresponding to each pixel.

From the light intensity detected at each pixel (and the associated angle of incidence of the light beams it receives), the reflectance at the prism/sample interface I can be calculated and the result represented as a graph of reflectance versus angle of incidence (or pixel), i.e. a reflectance graph. An exemplary reflectance graph is illustrated in FIG. 2. As can be seen, the graph exhibits 100% reflection (TIR) over a range of pixels corresponding to low angles of incidence relative to interface I (high angles of incidence relative to the normal) and then transitions sharply to a relatively low percentage value of reflectance. The determination of the refractive index of a sample is performed by locating the pixel where the transition from total to partial reflection occurs in the graph of FIG. 2 and using the associated angle of incidence, together with the critical angle equation (1) above, to solve for refractive index. A convenient way to locate the transition is to search for the region of pixels where the reflectance has the greatest slope or rate of change. Because of the limited pixel resolution of existing detectors, interpolation between the pixels is usually also required. The range of refractive index values that can be measured is a function of the range of angles of incidence of the light rays that reach the detector, and a function of the refractive index of the prism material. A typical range that can be measured is refractive indices from 1.3 to 1.7.

Those skilled in the art will appreciate that, although the reflectance graph is shown visually in FIG. 2 for illustrative purposes, it need not exist in that form. For example, it may merely be a collection of data in a computer which can be processed in the manner described herein.

With existing refractometers, a number of operating conditions may lead to a false result being reported. For example, the user may not have cleaned the prism adequately prior to loading the liquid sample. This can result in a mixture of materials at the prism/sample interface. Sometimes, the user simply forgets to load a new sample and, instead, accidentally performs a duplicate measurement on the previously loaded sample. Another difficulty arises when an insufficient quantity of liquid sample is placed in the prism dish. If the quantity of liquid in the dish is too small, the upper free surface (or meniscus) of the liquid sample may be close enough to interface I to reflect some of the light back into the system that ideally should not reach the detector. This will result in incorrect reflectances being calculated for the pixels receiving this additional light. Users may also attempt to measure samples that cannot be well characterized by a single refractive index, for example inhomogeneous materials like colloidal suspensions. Finally, users may attempt to measure samples that have refractive indices that are outside the range of refractive index that the instrument can measure.

Broadly, it is an object of the present invention to avoid shortcomings of existing refractometry and methods and systems. It is specifically contemplated that the invention should prevent users from making false measurements in all of the situations discussed above.

In accordance with one aspect of the present invention, a critical-angle refractometer which utilizes an in image of light reflected from an optical interface with a vessel containing a sample under test to determine an optical property of the sample, sample properties are evaluated to prevent improper testing of the sample. This evaluation includes establishing reflectance information associating the amount of reflection with locations in the image; and utilizing a plurality of properties of the reflectance information to determine if the vessel contains a proper sample under test.

Preferably, the properties include the point of transition from complete to partial reflection and at least one of the following: the average rate of change of reflectance as a function of position in the image in a predefined range of interest (ROI) about the point of transition; the maximum reflectance in the ROI; the minimum reflectance in the ROI; the range of reflectance in the ROI; and the average reflectance in the ROI.

BRIEF DESCRIPTION OF THE DRAWINGS

The foregoing brief description and further objects, features, and advantages of the present invention will be understood more completely from the following detailed description of a presently preferred, but nonetheless illustrative, embodiment in accordance with the present invention, with reference being hand to the accompanying drawings, in which.

DETAILED DESCRIPTION OF THE PREFERRED EMBODIMENT

Figure 1:
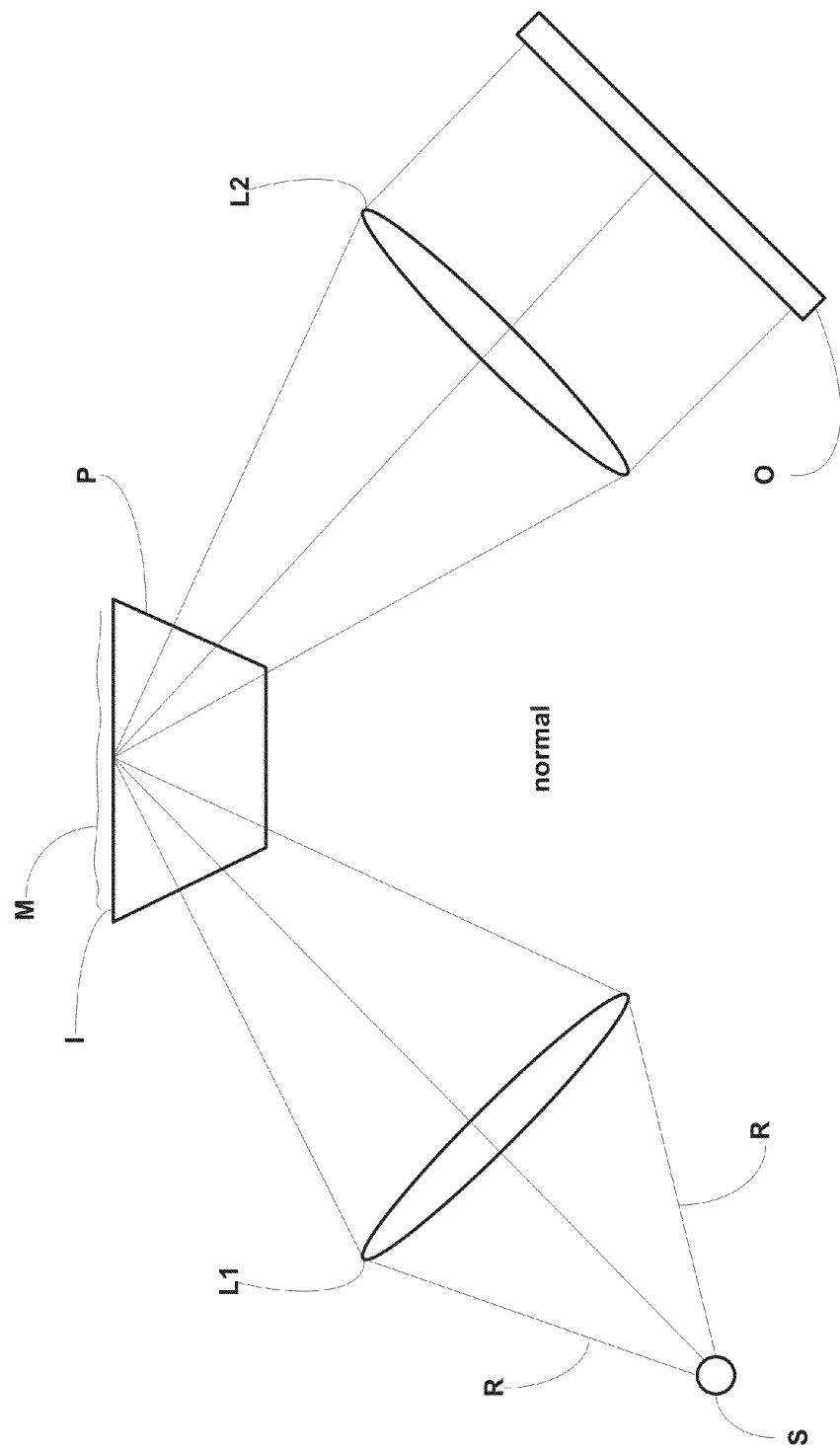
FIG. 1 is a schematic representation of a prior art critical-angle refractometer.
Figure 2:
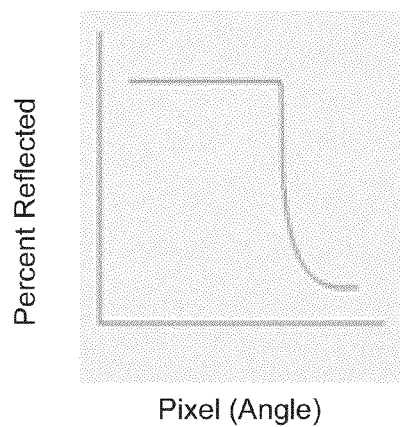
FIG. 2 is an exemplary reflectance graph obtained with a prior art prior art critical-angle refractometer.
Figure 3:
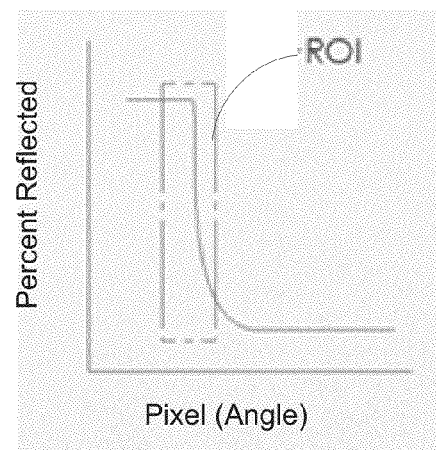
FIG. 3 illustrates a window or region of interest (ROI) established around the transition in a reflectance graph.

In addition to determining the refractive index by locating the pixel in the reflectance graph (e.g. FIG. 2) where the transition from total to partial reflection occurs, embodiments in accordance with the present invention also characterize the transition with three additional parameters determined from the pixels and their associated reflectances. After the transition pixel is determined, a window or region of interest (ROI) is established around the transition (see FIG. 3). The three additional parameters are: the average steepness or slope of the graph across the ROI (scaled to 100% for a perfect sample), the maximum reflectance in the ROI, and the minimum reflectance in the ROI. Equivalently, the range and average of reflectance across ROI may be used instead of the maximum and minimum.

In a preferred embodiment, these parameters are used to discriminate among four possible states at the prism/sample interface:

1. Sample Present
2. Dish Clean
3. Sample Index Out of Range
4. Other

Figure 4:
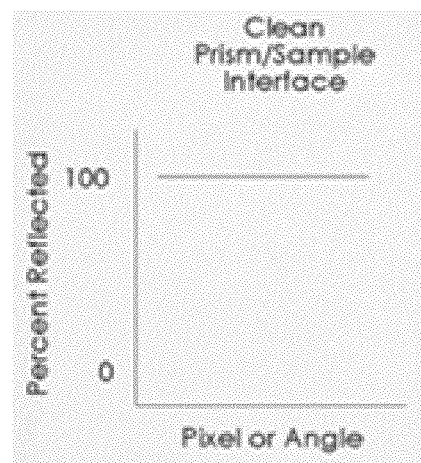
FIG. 4 illustrates the reflectance graph corresponding to a "Dish Clean" condition.

When the dish floor (interface I) is clean, all of the ray bundles undergo TIR at the prism/sample interface, and for each pixel across the detector a reflectance close to 100% is calculated. Such a graph is shown in FIG. 4. The transition region of interest, which is located by searching for the region of pixels where the reflectance has the greatest slope or rate of change, will be found at a random pixel determined by the noise in the signal. Since for this example all regions are the same, the location is not important to the analysis. The three parameters may be compared with stored preset values or thresholds as per the following example: If the reflectance range across the ROI is less than 5%, and the minimum reflectance is greater than 95%, and the average scaled slope is less than 5%, then the prism/sample interface state is "Dish Clean". In other words, this condition is characterized by a relatively constant reflectance range, a minimum reflectance above a high threshold and an average slope below a low threshold.

Figure 5:
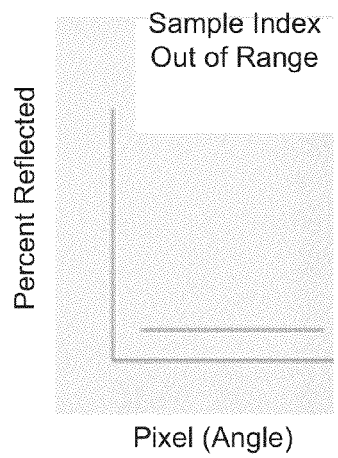
FIG. 5 illustrates the reflectance graph corresponding to a "Sample Index Out of Range" condition.
Figure 6:
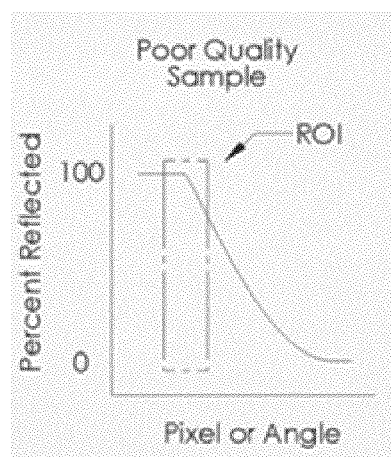
FIGS. 6 and 7 illustrate reflectance graphs corresponding to a "Sample Present" condition, with FIG. 6 illustrating a poor quality sample and FIG. 7 illustrating a normal quality sample.
Figure 7:
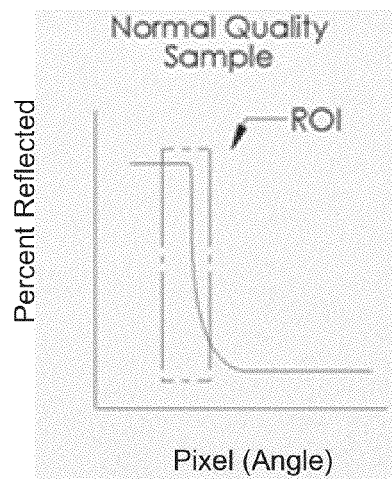

When the user loads a sample that has a refractive index that is above the range of the instrument, none of the ray bundles undergoes TIR at the prism/sample interface, and for each pixel across the detector a low reflectance is calculated. Such a graph is shown in FIG. 5. The transition region of interest, which is located by searching for the region of pixels where the reflectance has the greatest slope or rate of change, will again be found at a random pixel determined by the noise in the signal. Since for this example as well all regions are the same, the location is not important. The three parameters may be compared with stored preset values or thresholds as per the following example: If the reflectance range across the ROI is less than 5%, and the maximum reflectance is less than 5%, and the average scaled slope is less than 5%, then the prism/sample interface state is "Sample Index Out of Range". In other words, this condition is characterized by a relatively constant reflectance range, a maximum reflectance below a low threshold and an average slope below a low threshold When the user loads a sample that has a refractive index that is within the range of the instrument, some of the ray bundles undergo TIR at the prism/sample interface. Exemplary graphs are shown in FIGS. 6 and 7 for poor quality and normal quality samples, respectively. The transition region of interest is located by searching for the region of pixels where the reflectance has the greatest slope or rate of change. The three parameters may be compared with stored preset values or thresholds as per the following example: If the reflectance range across the ROI is greater than 20%, and the maximum reflectance is greater than 95%, and the average scaled slope is greater than 50%, then the prism/sample interface state is "Sample Present". In other words, this condition is characterized by a relatively large reflectance range (above a high threshold), a maximum reflectance above a high threshold and an average slope above a high threshold.

When the user loads a sample and a comparison of the three parameters with stored preset values does not satisfy the conditions for "Sample Present", "Dish Clean", or "Sample Index Out of Range"; then the prism/sample interface state is "Other". This may occur, for example, because scaled slope across the ROI has been lowered by lack of homogeneity in the sample or contamination at the prism/sample interface (see FIG. 7). It also may occur because additional light reflected from the sample meniscus has reduced the reflectance range across the ROI. Alternatively, the user may have only partially covered the interface with sample, so that more than one distinct refractive index is present at the boundary. This also will reduce the scaled slope over the ROI.

To prevent errors that are caused by the user forgetting to unload, clean, or reload the sample, the present invention also incorporates a computerized process (state machine) driven by the transitions in the prism/sample interface state. This "Message State" process provides instructions to the user in the form of indicators or messages displayed on a screen of the refractometer. The three Message States are:

1. Unloading
2. Loading
3. Measuring

"Unloading" is the initial Message State. An example Message State process is described by the following pseudo-code:

```
Start
Message State = "Unloading"
If the Message State is "Unloading"
    If the prism/sample interface state is "Other"
        Display message: "Sample quality is too low to measure.
        Please clean dish."
    If the prism/sample interface state is "Sample Present"
        Display message: "Please remove sample and clean dish."
        If the prism/sample interface state is "Sample Index Out of
        Range"
            Display message: "Sample index too high to measure.
            Please clean dish."
        If the prism/sample interface state is "Dish Clean"
            Transition to Message State "Loading"
    If the Message State is "Loading"
        Display message "Please load sample."
        If the prism/sample interface state is "Sample Present"
```

```
        Transition to Message State "Measuring"
    If the prism/sample interface state is "Other" or "Sample Index
    Out of Range"
        Transition to Message State "Unloading"
If the Message State is "Measuring"
    Display message "Measuring, please wait."
    If measurements are complete for this sample
        Transition to Message State "Unloading"
Go to Start
```

For proper operation of this algorithm it is understood that the prism/sample interface state transitions must be suitably debounced to give the operator time to clean the dish or load samples.

The software of the instrument can be configured to only allow measurement while the Message State is in the state "Measuring". This prevents the user from performing a measurement without unloading prior samples and cleaning the prism/sample interface. The user is also reminded to unload the sample after measurements are complete. A further benefit is that the measurement can be initiated automatically when the Message State transitions to "Measuring" so that the user is not required to press a button to start the measurement.

For differing types of samples, it is useful to adjust the stored preset values (thresholds) that are compared to the three parameters used to discriminate among the prism/sample interface states. For example, for a given sample it may be known a priori that the scaled slope over the ROI should never be below 80%, whereas for other samples it may be determined empirically that a lower value of scaled slope is acceptable. Therefore the present refractometer includes a database of named samples that includes user configurable fields to change the stored preset values used to discriminate among the prism/sample interface states.

Although a preferred embodiment of the invention has been disclosed for illustrative purpose, those skilled in the art will appreciate that many additions, modifications and substitutions are possible without departing from the scope and spirit of the invention, as defined by the accompanying claims.

What is claimed is:

1. A method for evaluating light reflected from a refractometer, having a vessel, to prevent improper testing of a sample, the method comprising the steps of:
   transmitting light from a light source toward an optical interface in the refractometer at a plurality of different angles of incidence;
   measuring an intensity of light reflected from the optical interface in response to said light transmissions at said different angles of incidence;
   determining reflectance information for the refractometer based on the light intensity measurements;
   evaluating, based on the determined reflectance information, whether one of operating conditions (a), (b), or (c), applies to the refractometer, wherein conditions (a), (b), and (c) refer to:
   (a) a sample being present;
   (b) the optical interface being clean; and
   (c) a measured refractive index being outside a range for the refractometer, respectively; and
   determining that a fourth operating condition "other" applies to the refractometer if none of conditions (a), (b), or (c) applies.

2. The method of claim 1 wherein properties of the reflectance information include the point of transition from complete to partial reflection and at least one of the following:
   a scaled average rate of change of reflectance as a function of position in the image in a predefined range of interest (ROI) about the point of transition;
   the maximum reflectance in the ROI;
   the minimum reflectance in the ROI;
   the range of reflectance in the ROI; and
   the average reflectance in the ROI.

3. The method of claim 1 further comprising a method for instructing an operator in handling the sample, characterized by the following pseudo-code:

```
Start
    Message State = "Unloading"
    If the Message State is "Unloading"
        If the prism/sample interface state is "Other"
            Display message: "Sample quality is too low to measure.
            Please clean dish."
        If the prism/sample interface state is "Sample Present"
            Display message: "Please remove sample and clean dish."
        If the prism/sample interface state is "Sample Index Out of
        Range"
            Display message: "Sample index too high to measure.
            Please clean dish."
        If the prism/sample interface state is "Dish Clean"
            Transition to Message State "Loading"
    If the Message State is "Loading"
        Display message "Please load sample."
        If the prism/sample interface state is "Sample Present"
            Transition to Message State "Measuring"
        If the prism/sample interface state is "Other" or "Sample Index
        Out of Range"
            Transition to Message State "Unloading"
    If the Message State is "Measuring"
        Display message "Measuring, please wait."
        If measurements are complete for this sample
            Transition to Message State "Unloading"
    Go to Start.
```

4. The method of claim 1 wherein measurement is automatically initiated when the sample properties evaluated transition from the optical interface being clean to the sample being present.

5. An apparatus for evaluating light reflected from a refractometer, having a vessel, to prevent improper testing of a sample, the apparatus comprising:
   a light source for transmitting light toward an optical interface in the refractometer at a plurality of different angles of incidence;
   a detector for measuring an intensity of light reflected from the optical interface in response to said light transmissions at said different angles of incidence;
   a computer for determining reflectance information based on the light intensity measurements; and
   a state machine for evaluating, based on the determined reflectance information, whether one of refractometer operating conditions (a), (b), or (c) applies to the refractometer, wherein conditions (a), (b), and (c) refer to:
   (a) a sample being present in the vessel;
   (b) the optical interface being clean; and
   (c) a measured refractive index being outside a range for the refractometer, respectively;
   wherein the state machine is also operable to determine that a fourth operating condition "other" applies to the refractometer if none of conditions (a), (b), or (c) applies.

6. The refractometer of claim 5 wherein properties of the reflectance information include the point of transition from complete to partial reflection and at least one of the following:
   a scaled average rate of change of reflectance as a function of position in the image in a predefined range of interest (ROI) about the point of transition;

the maximum reflectance in the ROI;
the minimum reflectance in the ROI;
the range of reflectance in the ROI; and
the average reflectance in the ROI.

7. The method of claim 5 further comprising a processor for instructing an operator in handling the sample, the processor operating in accordance with the following pseudo-code:

```
Start
    Message State = "Unloading"
    If the Message State is "Unloading"
        If the prism/sample interface state is "Other"
            Display message: "Sample quality is too low to measure.
                Please clean dish."
        If the prism/sample interface state is "Sample Present"
            Display message: "Please remove sample and clean dish."
        If the prism/sample interface state is "Sample Index Out
            of Range"
            Display message: "Sample index too high to measure.
                Please clean dish."
        If the prism/sample interface state is "Dish Clean"
            Transition to Message State "Loading"
    If the Message State is "Loading"
        Display message "Please load sample."
        If the prism/sample interface state is "Sample Present"
            Transition to Message State "Measuring"
        If the prism/sample interface state is "Other" or "Sample Index
            Out of Range"
            Transition to Message State "Unloading"
    If the Message State is "Measuring"
        Display message "Measuring, please wait."
        If measurements are complete for this sample
            Transition to Message State "Unloading"
    Go to Start.
```

8. The refractometer of claim 5 wherein the refractometer is further constructed to initiates measurement automatically when the sample properties evaluated transition from the optical interface being clean to the sample being present.

9. A method for evaluating light reflected from a vessel within a refractometer to prevent improper testing of a sample, the method comprising the steps of:

transmitting light at a plurality of angles of incidence from a light source towards an optical interface in the refractometer;

measuring an intensity of light reflected from the optical interface at a detector;

determining the reflectance at said angles of incidence based on said measured light intensity;

determining an operating condition of the refractometer based on at least one of the following reflectance parameters:

(a) the maximum reflectance within a region of interest (ROI) at a point of transition from complete to partial light reflection by the optical interface;

(b) the range of reflectance within the ROI; and (c) the average reflectance in the ROI; and wherein the step of determining the operating condition comprises evaluating whether one of conditions (i), (ii), or (iii) applies to the refractometer, wherein conditions (i), (ii), and (iii) refer to: (i) a sample being present; (ii) the optical interface being clean; and (iii) a measured refractive index being outside a range for the refractometer, respectively; and determining that a fourth operating condition "other" applies if none of conditions (i), (ii), or (iii) applies.

10. The method of claim 9 wherein the step of determining an operating condition is conducted based on (d) the minimum reflectance in the ROI and at least one of parameters (a), (b), (c) above.

11. The method of claim 9 further comprising:

determining that a sample is present in the refractometer if all of the following conditions are present:

the reflectance range across the region of interest is greater than about 20%;

the maximum reflectance is greater than about 95%; and the scaled average rate of change of reflectance is greater than about 50%.

\* \* \* \* \*